(12) United States Patent
Wallace

(10) Patent No.: US 6,315,768 B1
(45) Date of Patent: Nov. 13, 2001

(54) PERFUSION PROCEDURE AND APPARATUS FOR PREVENTING NECROSIS FOLLOWING FAILED BALLOON ANGIOPLASTY

(76) Inventor: Richard K. Wallace, 3358 N. Camino Los Brazos, Tucson, AZ (US) 85750

( * ) Notice: Subject to any disclaimer, the term of this patent is extended or adjusted under 35 U.S.C. 154(b) by 0 days.

(21) Appl. No.: 09/327,645

(22) Filed: Jun. 8, 1999

(51) Int. Cl.⁷ .................................................. A61M 31/00
(52) U.S. Cl. ............................................................. 604/507
(58) Field of Search ................................ 604/4–8, 50–54, 604/507–510, 4.01, 5.01, 6.01, 6.04, 6.11, 6.12, 6.15, 6.16

(56) References Cited

U.S. PATENT DOCUMENTS

| | | | |
|---|---|---|---|
| Re. 35,352 | * 10/1996 | Peters . | |
| 4,413,989 | * 11/1983 | Schjeldahl et al. | 604/96 |
| 4,857,054 | 8/1989 | Helfer | 604/102 |
| 4,921,483 | * 5/1990 | Wijay et al. | 604/96 |
| 5,011,469 | * 4/1991 | Buckberg et al. | 604/4 |
| 5,176,619 | 1/1993 | Segalowitz . | |
| 5,273,526 | * 12/1993 | Dance et al. | 604/35 |
| 5,486,192 | * 1/1996 | Walinsky et al. . | |
| 5,522,800 | * 6/1996 | Crocker | 604/96 |
| 5,746,709 | 5/1998 | Rom et al. | 604/8 |
| 5,807,331 | 9/1998 | Don Heijer et al. | 604/101 |
| 5,830,222 | 11/1998 | Makower | 606/159 |
| 5,833,650 | 11/1998 | Imran | 604/53 |

* cited by examiner

Primary Examiner—Richard K. Seidel
Assistant Examiner—Kevin C. Sirmons
(74) Attorney, Agent, or Firm—Antonio R. Durando; Durando Birdwell & Janke, PLC

(57) ABSTRACT

A perfusion catheter is used to avoid ischemia in case of failure of a conventional balloon angioplasty procedure on a stenotic blood vessel and a resulting partial or complete occlusion of the vessel. The balloon catheter is first removed from the vessel while the guide wire and the guide catheter are left in place. The perfusion catheter is immediately inserted into the guide catheter and run past the stenosis using the guide wire already in place. Blood is drawn from a side port in the sheath introduced at the point of entry into the vascular system of the patient under normal arterial pressure or after passing through an exterior pump for pressurization and re-injection in the perfusion catheter. Thus, blood flow to the part of the vessel past the occlusion can be reestablished within minutes of angioplasty failure and the patient can be stabilized in preparation for heart surgery.

12 Claims, 8 Drawing Sheets

PERFUSION PROCEDURE AND APPARATUS FOR PREVENTING NECROSIS FOLLOWING FAILED BALLOON ANGIOPLASTY

BACKGROUND OF THE INVENTION

1. Field of the Invention

This invention is related in general to the field of angioplasty treatment of atherosclerotic vessels in mammalian bodies. In particular, the invention pertains to a procedure for providing immediate blood flow through a blocked vessel following its collapse as a result of a failed angioplasty or stent placement.

2. Description of the Related Art

Angioplasty treatments of body vessels are invasive procedures whereby a catheter is inserted into the vascular system to reach and treat a partial or total occlusion causing reduced blood flow. Most notable is balloon angioplasty, where the distal end of the catheter includes an inflatable balloon that is used to expand the vessel and restore sufficient lumen size to ensure adequate blood flow after removal of the catheter.

This procedure has become very common in treating cardiovascular disease and is normally performed, when possible, as a preferable alternative to coronary bypass surgery. Similarly, the placement of a stent, a cylindrical wire mesh that is expanded in the area of stenosis to open and support a coronary artery, is always preceded by an angioplasty. As well understood in the art, the procedure involves placement of a balloon catheter through the locus of a stenosis, typically in a coronary artery, and inflation of the balloon to press against the material creating the occlusion. Because of the pressure exerted by the balloon, the vessel remains completely obstructed during the procedure, which normally lasts one to two minutes. During this time, blood flow through the vessel is essentially precluded and the heart tissue downstream of the blockage is dangerously deprived of oxygen. Therefore, cardiologists try and limit angioplasty procedures to the minimum time required to restore the stenotic passage to an acceptable size.

Various perfusion angioplasty catheters have been developed to enable the continued supply of blood during angioplasty and avoid the occurrence of ischemia. For example, U.S. Pat. Nos. 4,857,054, 5,746,709, 5,807,331 and 5,833,650 disclose various angioplasty catheters that include perfusion channels to produce blood flow past the stenosis during the angioplasty procedure. Some of these catheters utilize exterior, ex-vivo, pumps to create the pressure gradient necessary for blood flow through the catheter while the balloon is inflated. Others utilize sophisticated in-vivo systems of valves, pumps, and multiple balloons in the distal end of the catheter to control the direction of blood flow. While conceptually advantageous to provide an attractive solution to the problem of angioplasty-induced ischemia, these perfusion angioplasty catheters have met very little acceptance in the medical community. One problem is the increased size of such catheters with respect to conventional angioplasty catheters, which results from the added channels and apparatus required to perform the perfusion function within the lumen of the catheter. Other issues are greater cost and intricacy of use. Thus, most cardiologists continue to utilize conventional angioplasty catheters and strive to limit the time of the procedure as much as possible.

Sometimes, as a result of a coronary angioplasty or a stem placement, the arterial vessel collapses and blood flow to the heart is completely blocked, creating a severe, life-threatening emergency. Standard procedure in such situations requires the immediate performance of coronary bypass surgery. In fact, a patient found in such a predicament is rushed to the operating room in the hope of restoring oxygenation to the heart in time to save his or her life. Unfortunately, that is often not possible because of the time delay involved in reaching the affected artery. This invention is directed at solving this emergency problem.

BRIEF SUMMARY OF THE INVENTION

The primary objective of this invention is a method and apparatus for immediately restoring some degree of blood flow through a blood vessel that has become totally occluded as a result of a failed angioplasty or stent placement procedure.

Another important goal of the invention is a method and apparatus that provide sufficient blood flow through a collapsed stenosis to prevent ischemia and improve the chances of a patient for successful open-heart surgery.

Another objective of the invention is a procedure that can be implemented in conjunction with and immediately following conventional angioplasty or stent placement.

Still another objective is a procedure that utilizes existing angioplasty and perfusion catheters and related apparatus.

A final objective is a procedure that can be implemented easily and economically according to the above stated criteria.

Therefore, according to these and other objectives, the preferred embodiment of the present invention begins by utilizing a conventional catheter to perform a balloon angioplasty procedure on a stenotic blood vessel. In case of failure of the procedure and a resulting complete occlusion of the vessel, the balloon catheter is removed from the vessel while the guide wire and the guide catheter are left in place. A perfusion catheter is immediately inserted into the guide catheter and run past the stenosis using the guide wire already in place. Blood is drawn from a side port in the sheath introduced at the point of entry into the vascular system of the patient, typically along the femoral artery, and is passed into the perfusion catheter under normal arterial pressure. In the event of loss of arterial pressure, the blood so drawn is passed through an exterior pump for pressurization and re-injection in the perfusion catheter. Thus, blood flow to the part of the vessel past the occlusion can be reestablished within minutes of angioplasty or stent-placement failure and the patient can be stabilized in preparation for heart surgery.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

The present invention consists of a main inventive concept, the realization that the normal set up for a conventional balloon angioplasty is suitable for an emergency procedure to avoid ischemia in a patient in case of severe failure of the angioplasty. This concept of the invention provides immediate relief that makes it possible for a cardiologist to stabilize the patient in preparation for corrective heart surgery.

Figure 1:
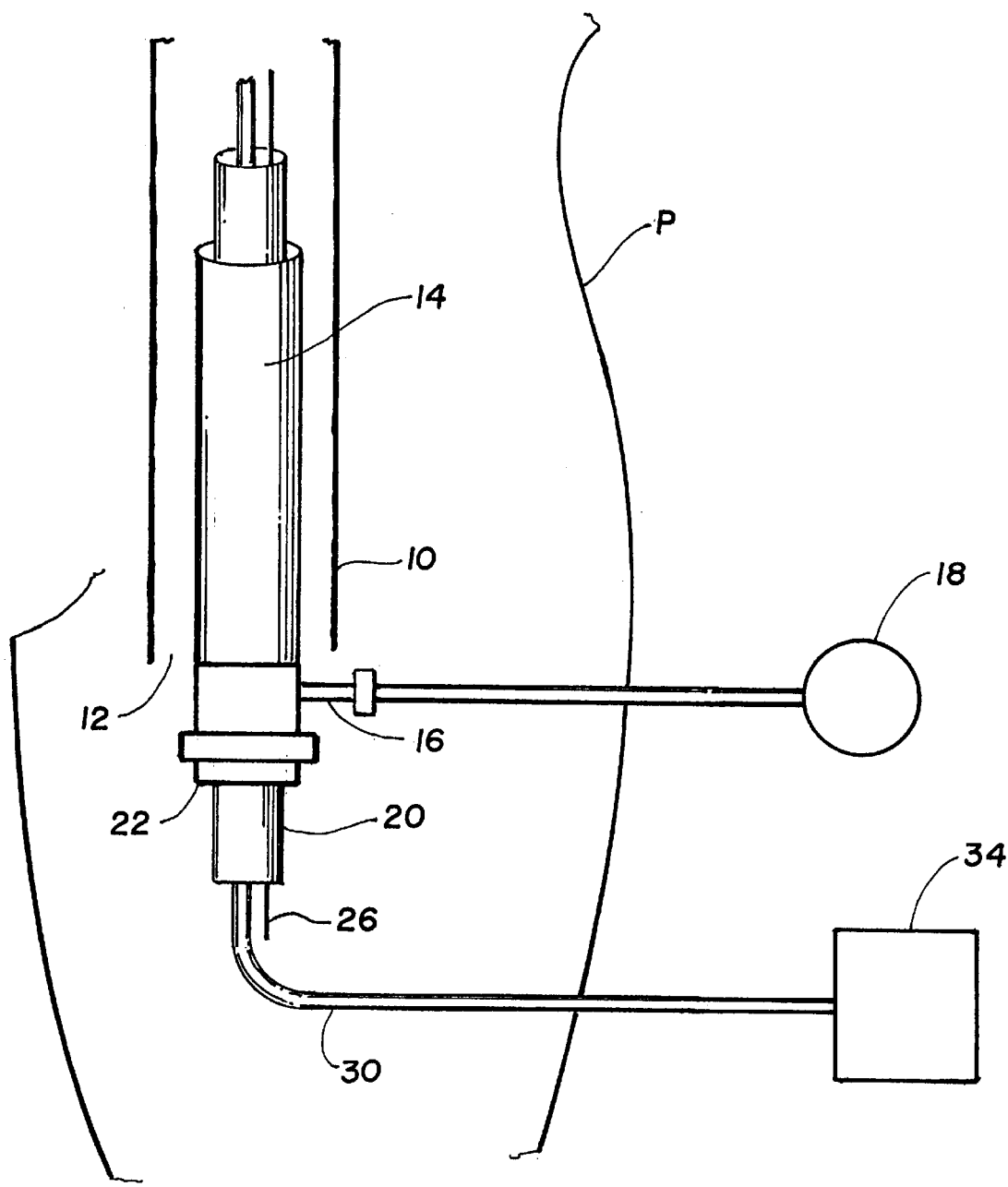
FIG. 1 is a schematic drawing illustrating the typical configuration of a catheter set up at the point of entry into the vascular system of a patient.

As used herein, the term "angioplasty catheter" is defined to refer to any catheter used in surgical procedures designed to enlarge the lumen of a vessel at the site of a stenosis. Referring to the drawings, wherein like parts are designated throughout with like numerals and symbols, FIG. 1 illustrates the typical set up used for conducting a balloon angioplasty procedure on a patient P. Access to a blood vessel 10, normally a femoral artery, is obtained percutaneously through an incision 12 in the groin area of the patient by inserting a sheath 14 having a diameter compatible with the size of the vessel and the size of the catheter to be used in the procedure. The sheath 14, in a portion external to the incision 12, includes a side port 16 for withdrawal of blood for periodic sampling, if tests are requires, and for monitoring the patient's blood pressure by an appropriate pressure gauge 18.

Figure 2:
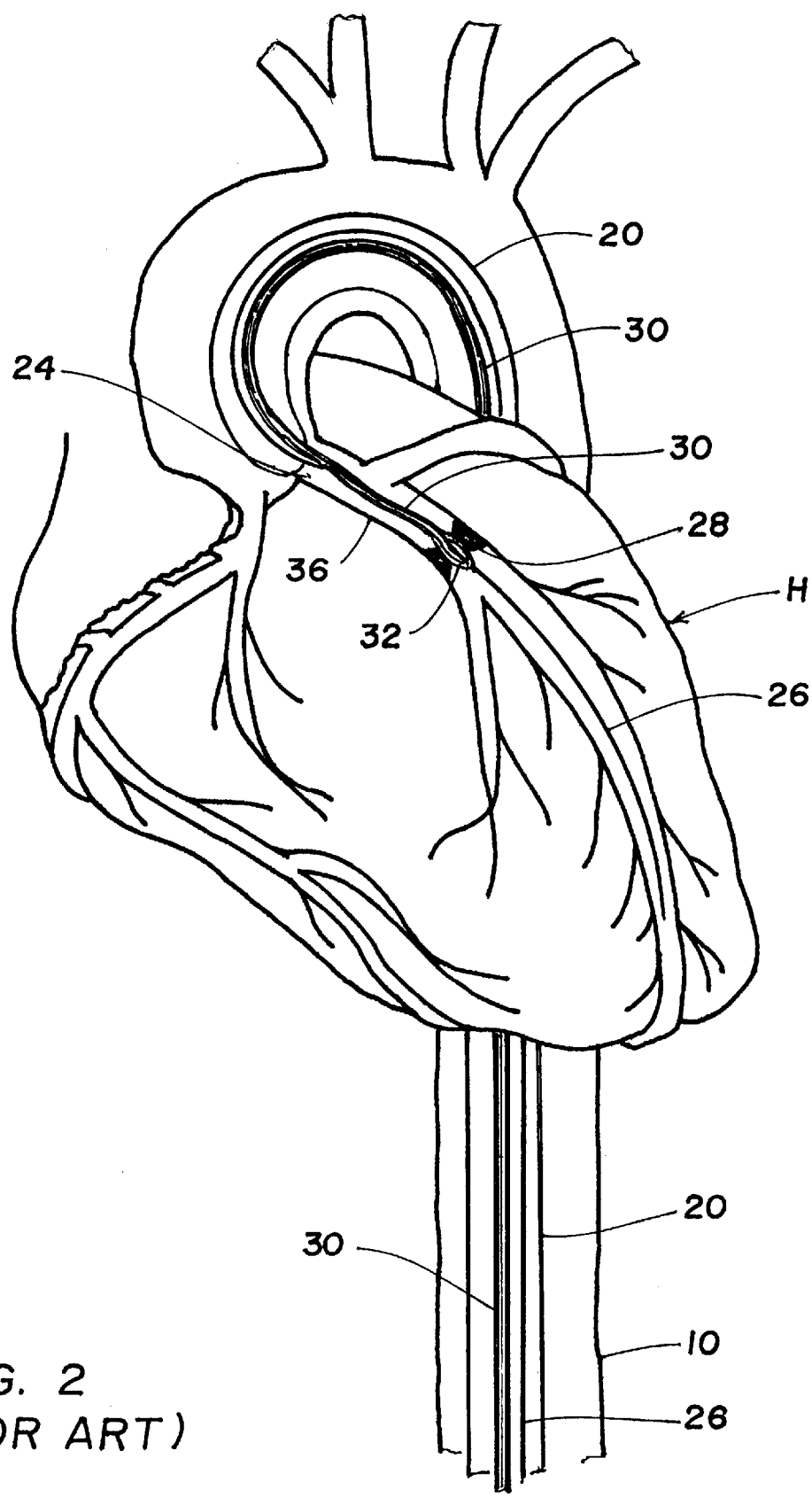
FIG. 2 is a schematic drawing illustrating a balloon angioplasty catheter, a guide catheter, and a guide wire extended through the femoral artery and aorta of a patient to the site of a stenosis in a coronary artery.
Figure 3:
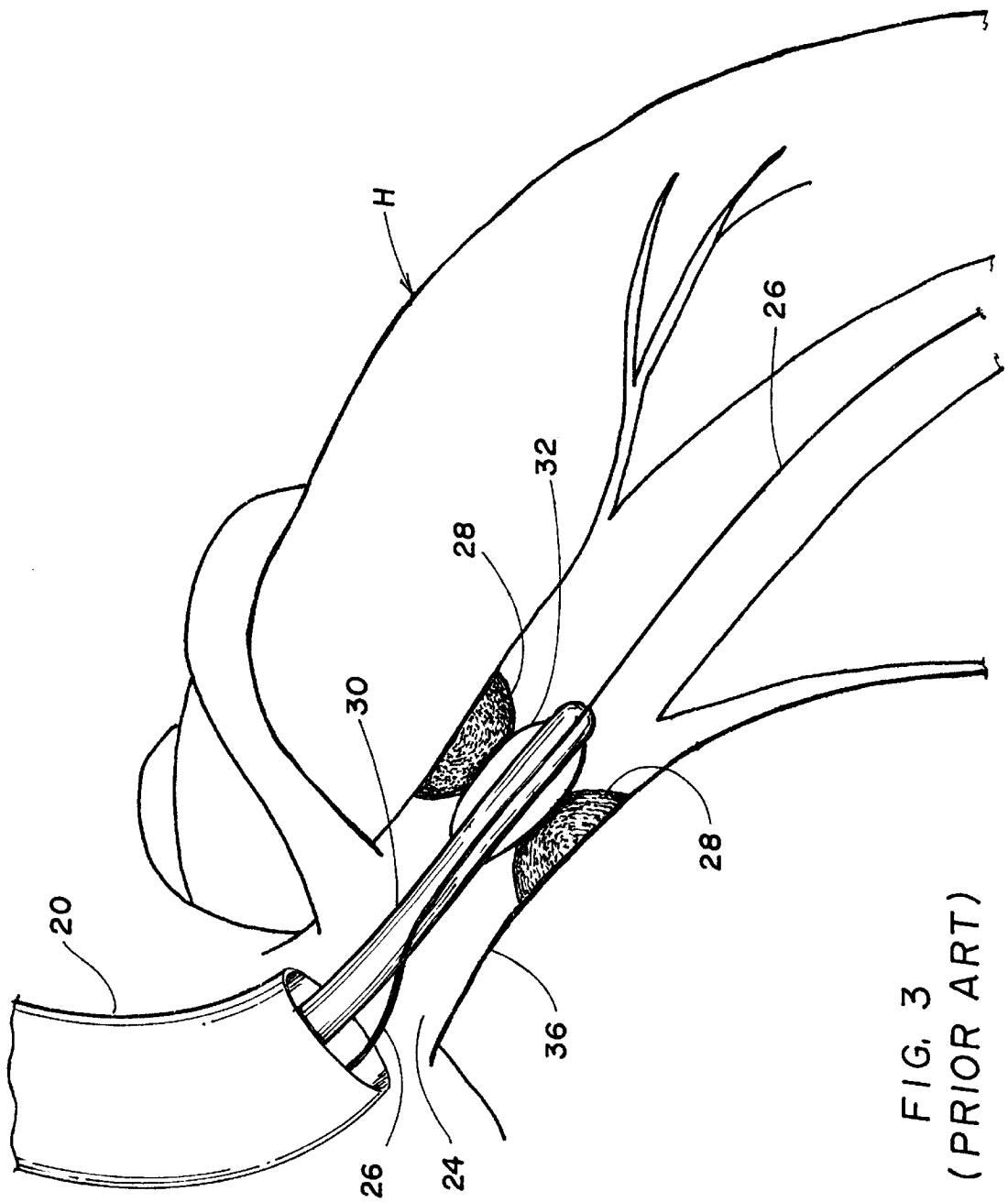
FIG. 3 is an enlarged schematic drawing illustrating a balloon angioplasty catheter apparatus in use at the site of a stenosis in a coronary artery.

The angioplasty procedure involves the introduction of a guide catheter 20 into the vessel 10 through an exterior main port 22 of the sheath 14. As shown in FIG. 2, the guide catheter 20 is run up the femoral artery all the way to the heart H, to the osteum 24 of the artery that contains the stenosis to be treated (the left coronary artery is shown for illustration). Once the guide catheter 20 is in place, a guide wire 26 is threaded through the guide catheter into the occluded vessel 10 and past the stenosis 28. Using the guide wire, a balloon catheter 30 is then passed over the guide wire through the guide catheter and placed with its tip past the stenosis 28 such that the balloon 32, incorporated in the distal end of the catheter, overlaps the occlusion. As illustrated in FIG. 3, the balloon 32 is then inflated by means of a fluid pumped into the balloon catheter 30 through appropriate control means 34 (FIG. 1) to expand the lumen of the artery 36 at the site of the stenosis 28. Obviously, blood flow through the artery 36 is essentially stopped while the balloon 32 is inflated. After treatment, the balloon is deflated and the catheter 30 is extracted using the guide catheter as a protective sleeve and the guide wire as a directional rail. The guide catheter and the guide wire are both left in place during the removal of the balloon catheter.

The intent of the angioplasty procedure is that, upon deflation of the balloon 32 and removal of the catheter 30, the enlarged opening at the site of the stenosis in the artery remain expanded and permit normal blood flow. If a stent is to be placed in the artery, the procedure follows the angioplasty and is carried out using the same guide wire 26 and guide catheter 20 used for the angioplasty. In some instances, though, one of these procedure is not successful and the artery occludes and produces a total blockage that could result into severe and life-endangering ischemia of heart tissue. Immediate action is necessary to save the life of the patient.

Figure 4:
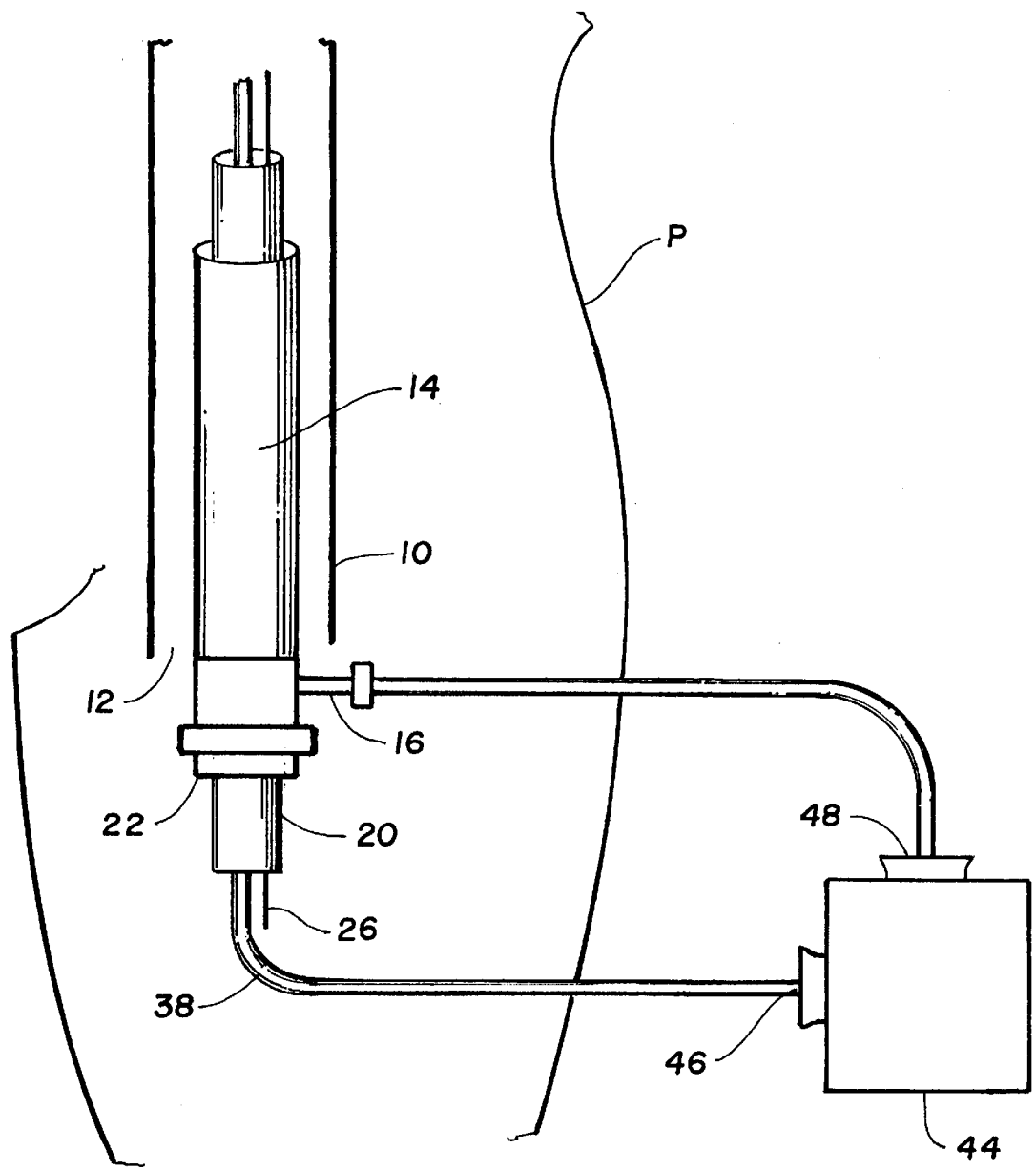
FIG. 4 is a schematic drawing illustrating the ex-vivo set up of the invention at the point of entry into the vascular system of a patient.
Figure 5:
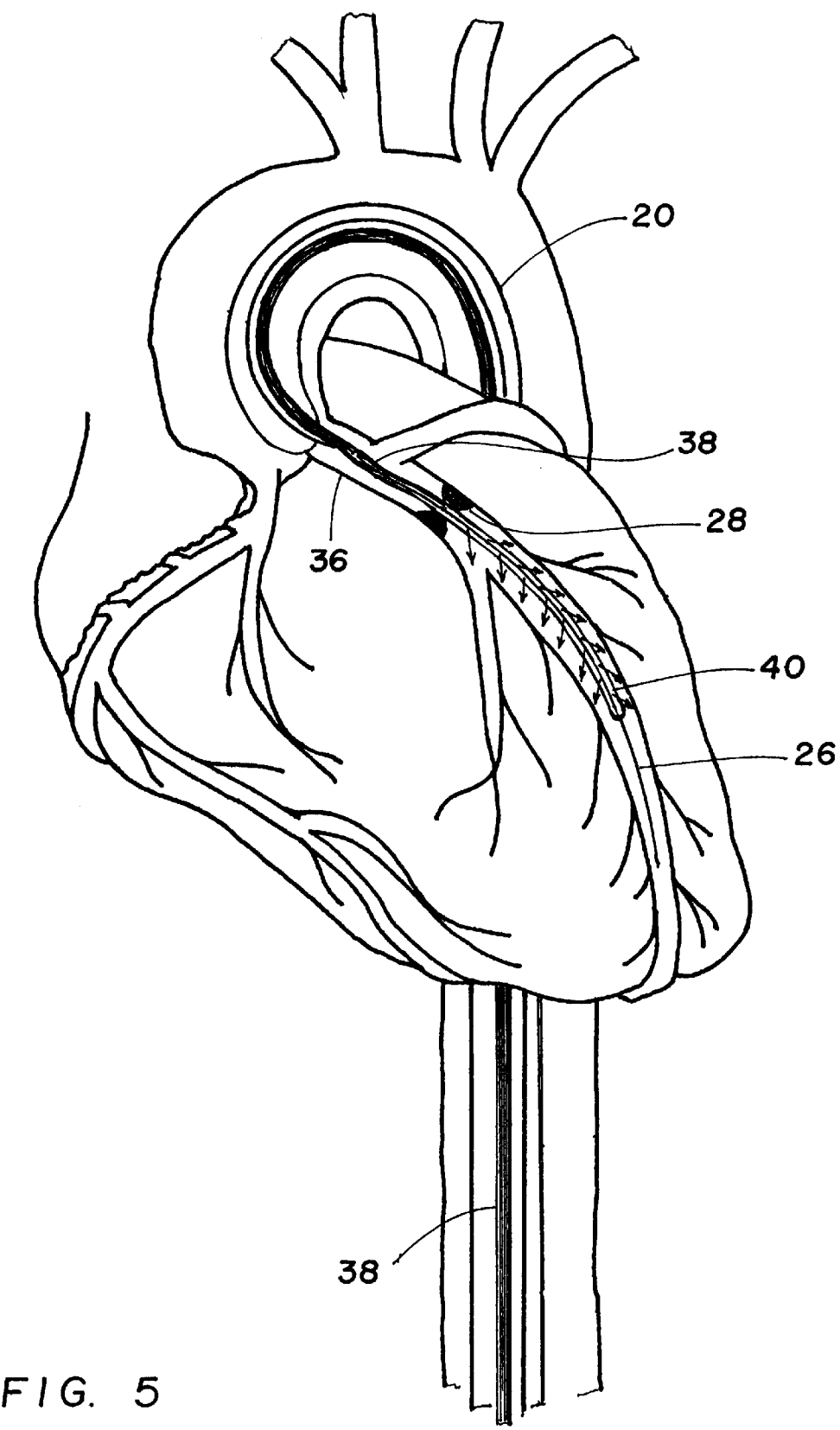
FIG. 5 is a schematic drawing illustrating the placement of a perfusion catheter through a patient's occluded coronary artery following failure of a balloon angioplasty procedure.
Figure 6:
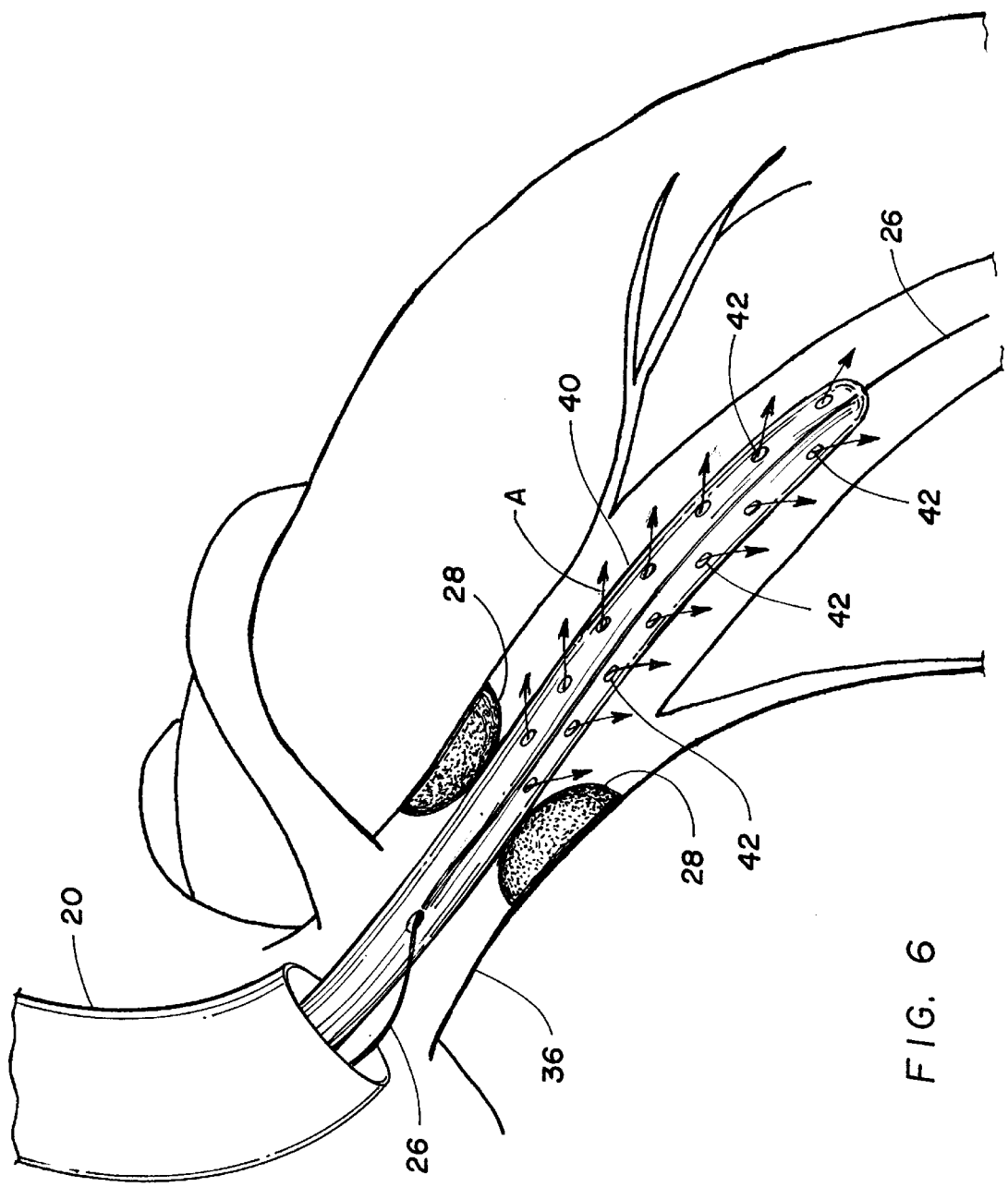
FIG. 6 is an enlarged schematic drawing illustrating the perfusion catheter of the invention in use at the site of a stenosis in a coronary artery.

According to the present invention, a conventional perfusion catheter is immediately introduced into the guide catheter 20 and run all the way past the stenosis 28 using the guide wire 26 already in place, as illustrated in FIGS. 4–6. In essence, a perfusion catheter 38 is used in replacement of the balloon catheter 30 within the system already in place in the patient P. Because the distal end of the guide wire 26 remains in the artery 36 past the site of the stenosis 28, the advancement of the perfusion end 40 of the perfusion catheter past the occlusion is easily accomplished simply by pushing it through, as shown in FIG. 6. As would be clearly understood by one skilled in the art, the end 40 needs to be advanced such that the perfusion orifices 42 distributed throughout its distal end 40 are beyond the vessel occlusion for injection of blood into that area of the artery 36.

Passage of blood through the perfusion catheter is effected by normal arterial pressure or by a pump 44 connected to the external proximal end 46 of the perfusion catheter, as seen in FIG. 4. A separate arterial line may be tapped as a source for the perfusion catheter but, in the preferred embodiment of the invention, the suction side of the perfusion pump 44 is connected to the side port 16 which is already in place and available to provide arterial blood for perfusion beyond the arterial blockage area, as indicated by the arrows A shown in FIG. 6. As such, a system is readily in place to transform conventional balloon angioplasty apparatus into an emergency perfusion device for combatting arterial occlusions resulting from the angioplasty. Typically, a pump capable of delivering 40–60 cc/min through the perfusion end 40 is adequate to practice the invention. This system provides immediate blood flow to the heart of the patient during the critical time after a failed angioplasty and before coronary artery bypass surgery is possible. In addition, through the external pump 44, blood can continue to be perfused into the distal portion of the artery 36 even when the patient experiences low blood pressure or ventricular dysrhythmias. This property greatly reduces the risk of heart tissue ischemia, cardiac failure, and even death.

Figure 7:
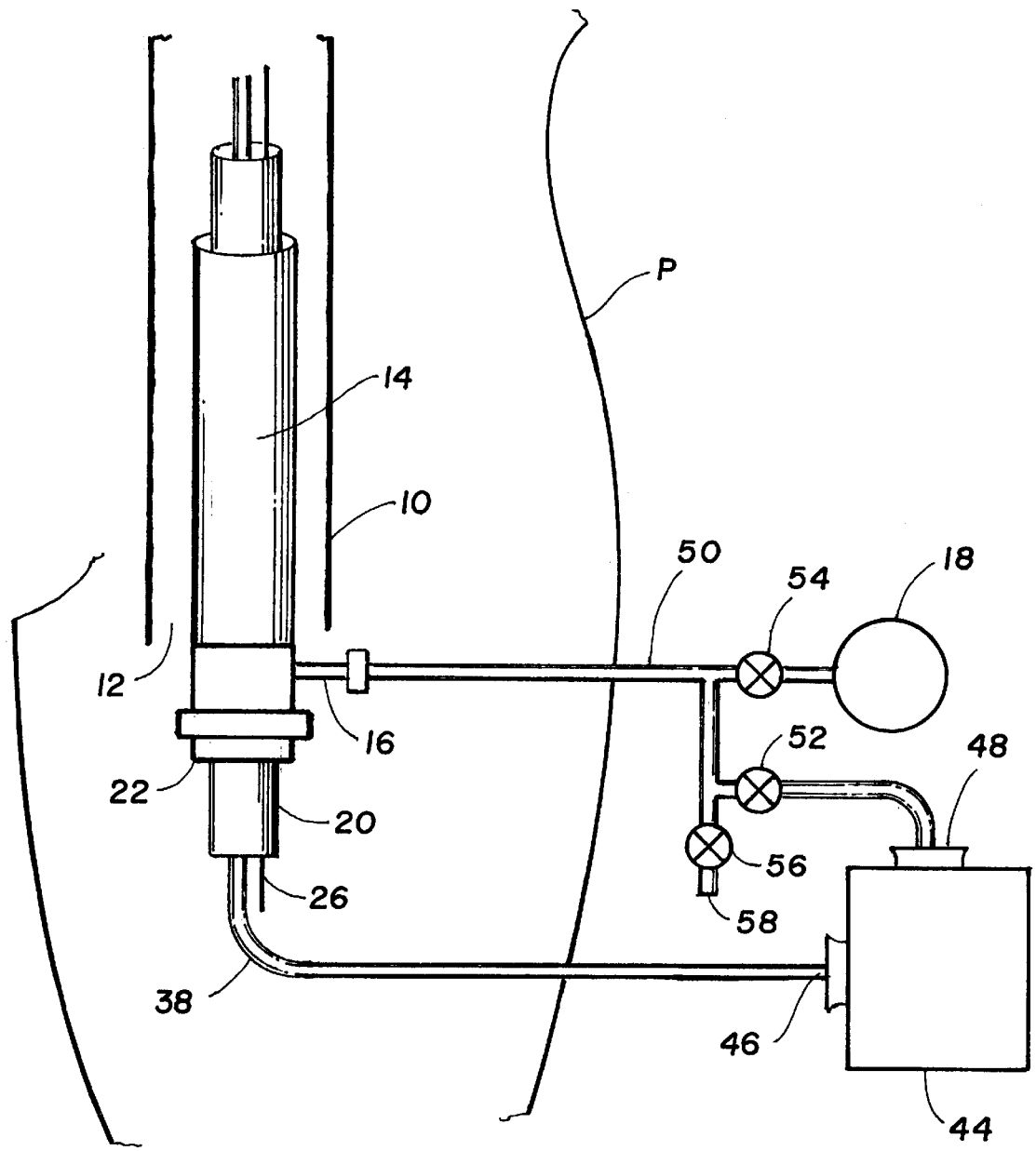
FIG. 7 is a schematic drawing of another embodiment of the invention showing the contemporaneous use of a side port for monitoring as well as supplying arterial blood to a perfusion pump.

Since the possibility of failure of an angioplasty or stent-placement procedure is always contemplated, a preferable arrangement, illustrated in FIG. 7, consists of coupling the intake 48 of pump 44 to the line 50 already connected to the side port 16 for monitoring purposes, so that a source of arterial blood is already hooked up for perfusion during the angioplasty procedure. Appropriate valves 52 and 54 are provided to control or switch the blood flow between the pump 44 and the monitoring equipment 18. An additional valve 56 and port 58 may be provided to alternatively connect the perfusion catheter 38 directly to the line 50 (i.e., bypassing the pump 44), if sufficient arterial pressure is present for perfusion at the desired rate.

Figure 8:
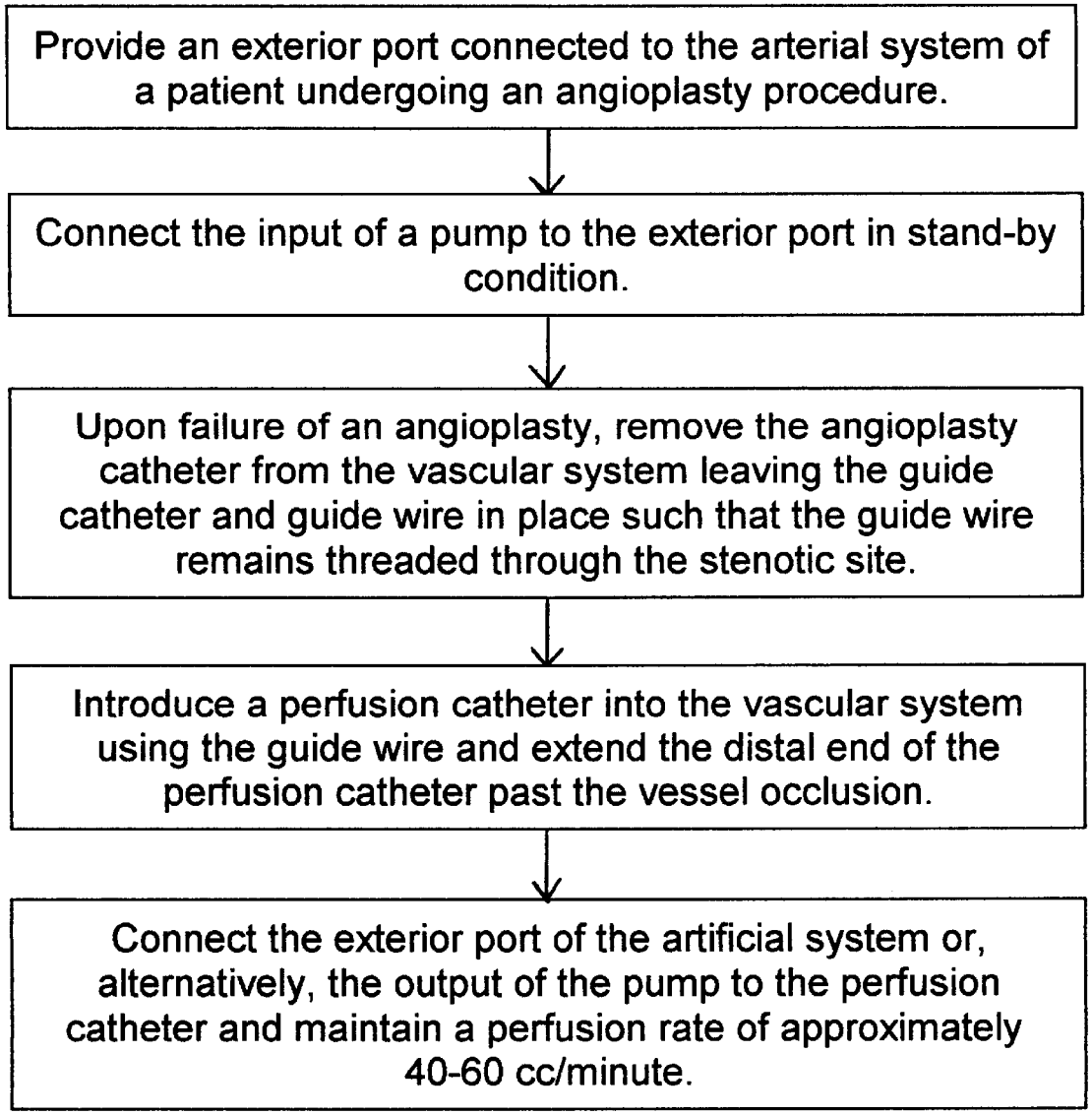
FIG. 8 is a flow chart of the steps of the invention.

The steps of the procedure of the invention are illustrated in the chart of FIG. 8 in the context of perfusion following a failed angioplasty.

Various changes in the details, steps and components that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

What is claimed is:

1. A method for maintaining a blood supply past a stenotic site after failure of a procedure wherein an angioplasty catheter is introduced into a blood vessel of a patient through a guide catheter contained in the vessel and on a guide wire extended through the stenotic site, and wherein a vessel occlusion along the guide wire occurs following retraction of the angioplasty catheter from the site, said method comprising the following steps:

(a) completely removing the angioplasty catheter from the vessel;

(b) introducing a perfusion catheter into the vessel of the patient through said guide catheter and extending a distal end of the perfusion catheter past the vessel occlusion using the guide wire, wherein the guide catheter has an extraction port connecting through a proximal segment and into the interior of said perfusion catheter;

(c) providing means for extracting the patient's blood from said extraction port; and (d) injecting blood into an exterior end of the perfusion catheter such as to maintain a perfusion rate sufficient to prevent ischemia.

2. The method of claim 1, wherein said perfusion rate is 40–60 cc/min.

3. The method of claim 1, wherein the step of injecting blood is carried out by withdrawing the patient's blood and passing it through a pump having an output connected to said exterior end of the perfusion catheter.

4. The method of claim 3, wherein said perfusion rate is 40–60 cc/min.

5. The method of claim 3, further including the step of providing an extraction port connected to a proximal segment of the guide catheter and wherein the step of injecting blood is carried out by connecting an input of said pump to said extraction port.

6. The method of claim 5, wherein said perfusion rate is 40–60 cc/min.

7. The method of claim 6, wherein said patient's blood is arterial blood.

8. The method of claim 3, wherein said patient's blood is arterial blood.

9. The method of claim 1, further including the step of providing an extraction port connected to a proximal segment of the guide catheter and wherein the step of injecting blood is carried out by connecting an input of a pump to said extraction port and an output of the pump to said exterior end of the perfusion catheter.

10. The method of claim 9, wherein said perfusion rate is 40–60 cc/min.

11. The method of claim 1, wherein said procedure is an angioplasty.

12. The method of claim 1, wherein said procedure is a stent placement.

* * * * *